(12) United States Patent
Notari et al.

(10) Patent No.: US 7,462,206 B2
(45) Date of Patent: Dec. 9, 2008

(54) USE OF A MIXTURE OF ESTERS OF FATTY ACIDS AS FUEL OR SOLVENT

(75) Inventors: Marcello Notari, Parma (IT); Franco Rivetti, Milan (IT)

(73) Assignee: Polimeri Europa S.p.A., Brindisi (IT)

( * ) Notice: Subject to any disclaimer, the term of this patent is extended or adjusted under 35 U.S.C. 154(b) by 627 days.

(21) Appl. No.: 10/525,793

(22) PCT Filed: Nov. 20, 2003

(86) PCT No.: PCT/EP03/13027

§ 371 (c)(1),
(2), (4) Date: Feb. 25, 2005

(87) PCT Pub. No.: WO2004/052874

PCT Pub. Date: Jun. 24, 2004

(65) Prior Publication Data

US 2005/0261144 A1  Nov. 24, 2005

(30) Foreign Application Priority Data

Dec. 12, 2002 (IT) .......................... MI2002A2627

(51) Int. Cl.
*C10L 1/18* (2006.01)

(52) U.S. Cl. ...................................... 44/388

(58) Field of Classification Search ................ 508/344, 508/462; 554/165; 44/387, 388
See application file for complete search history.

(56) References Cited

U.S. PATENT DOCUMENTS

| 2,967,173 A | | 1/1961 | Fang | |
| 4,032,550 A | * | 6/1977 | White et al. | ................ 554/165 |
| 4,695,411 A | | 9/1987 | Stern et al. | |
| 4,885,104 A | * | 12/1989 | Sturwold | .................... 508/344 |

FOREIGN PATENT DOCUMENTS

| EP | 1 126 011 | 8/2001 |
| WO | 93/09111 | 5/1993 |

OTHER PUBLICATIONS

Mouloungui Z., Pelet S.: "Study of the acyl transfer reaction: Structurenand properties of glycerol carbonate esters" European Journal of Lipid Science and Technology, vol. 103, pp. 216-222, 2001.

* cited by examiner

*Primary Examiner*—Glenn Caldarola
*Assistant Examiner*—Taiwo Oladapo
(74) *Attorney, Agent, or Firm*—Oblon, Spivak, McClelland, Maier & Neustadt, P.C.

(57) ABSTRACT

The invention relates to the use of a mixture, comprising one or more alkyl esters of fatty acids and one or more esters of fatty acids of glycerol carbonate, as a fuel or solvent.

6 Claims, No Drawings

USE OF A MIXTURE OF ESTERS OF FATTY ACIDS AS FUEL OR SOLVENT

The present invention relates to the use of a mixture, comprising one or more alkyl esters of fatty acids and one or more esters of fatty acids of glycerol carbonate, as a fuel or solvent.

More specifically, the present invention relates to the use of the above mixture as a fuel for diesel engines or as a conventional, industrial solvent.

The use as fuel for diesel engines of mixtures of alkyl esters, in particular methyl esters, of fatty acids, deriving from raw materials of a natural origin, mainly vegetable, such as soybean and rapeseed oils, is well known in the state of the art (so-called bio-diesel: Bio-resource technology, 70, Jan. 15, 1999). The use of bio-diesel has been widely accepted as a result of the considerable advantages it offers, both from an environmental (use of renewable raw materials, general reduction of exhaust emissions, absence of sulfur) and also motoristic point of view (increased lubricity).

Bio-diesel is obtained together with glycerol through the transesterification of oils or natural fats, consisting of triglycerides of fatty acids, with an alcohol, usually methanol or ethanol:

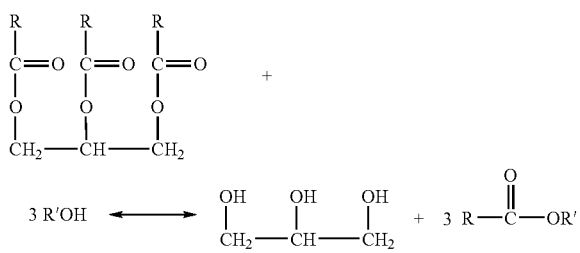

wherein:
R represents a linear, mono- or polyunsaturated alkyl or alkenyl radical, containing from 8 to 22 carbon atoms;
R' represents a linear or branched alkyl radical containing from 1 to 8 carbon atoms, preferably a methyl or ethyl radical.

The high co-production of glycerol, however, linked to the production of bio-diesel (over 100 g/kg of bio-diesel) represents a considerable technical and economic burden.

On the one hand, glycerol is not adequately placed or fully exploited on the market, which is even more so with the increase in the production and use of bio-diesel; on the other hand, the presence of residual glycerol, as such and as mono-, di- and triglycerides, in bio-diesel is not tolerated, due to problems of de-mixing and fouling.

For the above reasons, it has been necessary to establish narrow specification ranges: in practice, the free glycerol content in bio-diesel must be lower than 0.02% by weight, and the total glycerol, i.e. both in free form and partially or totally esterified, must be lower than 0.25% by weight. Complex separation and purification operations are therefore required to meet these specifications.

It has now been found that it is possible to conveniently use, as fuel or solvent, mixtures comprising one or more alkyl esters of fatty acids (bio-diesel) and one or more esters of fatty acids of glycerol carbonate.

The use of these mixtures as fuel or solvent is particularly interesting as they can be obtained through a process which allows the reuse of the glycerol co-produced together with the production of bio-diesel.

An object of the present invention therefore relates to the use as a fuel or solvent, of a mixture comprising one or more alkyl esters of fatty acids having formula (I):

RCOOR' and one or more esters of fatty acids of glycerol carbonate having formula (II):

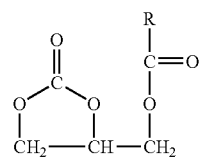

wherein:
R represents a mono- or polyunsaturated, linear, branched or cyclic alkyl or alkenyl radical, containing from 4 to 24 carbon atoms, preferably from 8 to 22 carbon atoms;
R' represents a linear, branched or cyclic alkyl radical containing from 1 to 8 carbon atoms, preferably a linear or branched $C_1$-$C_4$ radical, more preferably a methyl or ethyl radical.

The esters of fatty acids of glycerol carbonate are preferably present in the mixture in a weight percentage ranging from 10 to 40%.

Examples of these esters are represented by the esters of caprylic, lauric, myristic, palmitic, stearic, oleic, linoleic, linolenic acids, or mixtures thereof.

Fats and oils of a natural origin, mainly of vegetable origin, are conveniently used as sources of the above esters, such as, for example, rapeseed oil, soybean oil, palm oil, coconut oil, sunpourer oil, peanut oil, cotton seed oil, sesame oil, or exhausted oils used as food.

The mixtures object of the invention have proved to be suitable for use as fuels in diesel cycle engines, from a combustion and motoristic point of view, in general. These mixtures typically have net heat values equal to 36-37 MJ/kg and cetane number values higher than 49, values which are entirely similar to those of conventional bio-diesel.

These mixtures have proved to be particularly efficient in the reduction of pollutant emissions, such as carbon monoxide, sulfur dioxide, benzene and the other incombusted hydrocarbon and particulate, due to their high oxygen content (from 12% to 15% weight), higher than that of conventional bio-diesel (about 10% weight) and the absence of sulfur content.

The mixtures, object of the invention, also have unique solvent characteristics, which makes them a highly eco-compatible solvent, non-flammable, with a high boiling point and low toxicity, suitable for substituting conventional industrial solvents, such as limonene and solvents of a petroleum origin, currently used in a wide range of applications.

Examples of applications are the removal of oils and fats from engines, metal manufactured products, furnaces; degreasing of leather; adhesive and ink removal; use as releasing agent in the moulding of metal and cement manufactured products; use as solvent and lubricant in metal cutting operations; use as solvent in oil-based paintings.

Alkyl esters of fatty acids (conventional bio-diesel) can be further added to the mixtures, object of the invention, for their use according to the purposes of the invention.

When adopted as a solvent, the mixtures can be used as such or formulated with other components such as water and surfactants, whereas when used as fuel for diesel cycle engines, they can be used as such or added to mineral gasoil, for example by adding 5-30 parts in volume of said mixtures to 95-70 parts in volume of gasoil, according to what is known in the state of the art for the use of bio-diesel.

These formulations can also include conventional quantities of additives for enhancing the cetane number, such as peroxides or nitrates, additives for lowering the pour point and for controlling the viscosity and lubricity, stabilizers, detergents, antioxidants, compatibilizing agents.

The mixtures of the invention are obtained in a simple and convenient way, by reaction (transesterification) of one or more esters of fatty acids of glycerol, in particular a triglyceride, or a mixture of triglycerides of fatty acids, such as those contained in oils and fats of a natural origin, with one or more alkyl carbonates, in the presence of a base catalyst, for example by means of the process described in international patent application WO 93/09111:

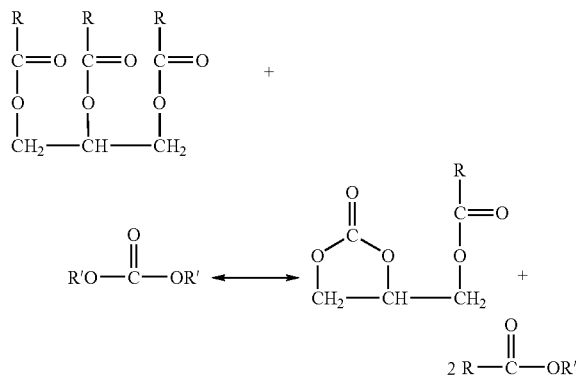

wherein R, the same or different, and R', again the same or different, have the above-mentioned meanings.

The reaction is carried out in the presence of a catalyst, homogeneous or heterogeneous in the reaction medium, consisting of an organic or inorganic base.

Examples of bases which can be used are alkoxides or carbonates of alkaline metals, such as, for example, sodium methylate or potassium tert-butoxide; a guanidine or cyclic guanidine; a hydrotalcite.

The catalyst is generally used in a molar quantity ranging from 1 to 10%, with respect to the ester of glycerol used in the reaction.

The oil and fat of a natural origin and the dialkyl carbonate, used as reagents, must have a low water content, above all when the catalysts used are alkoxides or carbonates of alkaline metals. Water, in fact, favours a saponification side-reaction producing soaps which lower the yield of the transesterification reaction.

The water is preferably extracted from the reagents, which is effected, when necessary, before the addition of the catalyst, by means of azeotropic distillation with an organic azeotrope-forming solvent, for example a dialkyl carbonate such as dimethyl carbonate (DMC) or diethyl carbonate (DEC), a hydrocarbon such as cyclohexane, hexane, heptane or toluene, an ether, such as tert-butyl methyl ether or ethyl ether.

When the dialkyl carbonate used in the synthesis of the mixture of the invention is DMC or DEC, the azeotrope-forming solvent is the dialkyl carbonate itself.

The azeotropic distillation is generally carried out using a quantity of azeotrope-forming solvent ranging from 2% to 15% by weight of vegetable oil at a temperature ranging from 50° C. to 150° C. and at a pressure ranging from 0.2 Ata to 6 Ata.

The oil or fat of a natural origin should have a low content of free fatty acids, preferably not higher than 1 mg KOH/g, to avoid the excessive consumption of catalyst and excessive formation of soaps which reduce the transesterification yield.

The reaction is generally carried out at a temperature ranging from 60° C. to 150° C. for times varying from 1 to 24 hours, using a molar ratio of the alkyl carbonate with respect to the ester of glycerol used in the reaction ranging from 1 to 6.

The alkyl carbonate is preferably used in excess as it also acts as reaction solvent. The reaction can be carried out batchwise, in semi-continuous or in continuous in a nitrogen atmosphere or under autogenous pressure, generally ranging from 1 Ata to 6 Ata.

The product is isolated and purified using conventional techniques such as neutralization and subsequent removal of the catalyst by filtration or separation of the catalyst in a de-mixed liquid phase; the possible removal of the excess of alkyl carbonate by distillation; washing with water or aqueous acids; extraction with an organic solvent, for example a hydrocarbon such as hexane, cyclohexane or heptane, an ether such as ethyl ether or tertbutyl methyl ether, a dialkyl carbonate.

When the triglycerides used in the reaction are those present in oils of a vegetable origin, such as soybean oil or rape oil, the mixtures, object of the invention, are liquid at room temperature and can be mixed in all proportions with the hydrocarbons and oil distillates, such as gasolines and gasoil in particular.

The following examples are provided for illustrative purposes and do not limit the scope of the present invention.

In these examples, the transesterification reaction is carried out in a jacketed glass reactor, having a volume of 5 liters, heated by circulation in the jacket of oil coming from a thermostat-regulated bath. Said reactor is equipped with a water-cooled condenser, a mechanical stirrer, a thermometer, a plunge-pipe for collecting samples and a glass distillation column with 15 perforated plates, having an internal diameter of 2.5 cm. All the vapour is condensed at the head of the column and only a part of the liquid is removed, at the reflux ratio established by the intervention of an electromagnetic valve.

EXAMPLE 1

The following reagents are added to the reactor described above: 2042 g (2.34 moles) of soybean oil and 782 g of dimethyl carbonate. The stirring is activated and the reactor is heated with an oil bath thermostat-regulated at 115° C. In order to eliminate the water from the reagents, 150 g of dimethyl carbonate are distilled with a reflux ratio equal to 2. The mixture is left to cool to room temperature which now contains 632 g of dimethyl carbonate (7.02 moles) and 21.6 g of a solution of sodium methoxide at 30% by weight in methanol (0.12 moles of sodium methoxide) are added. The reactor is heated again so as to obtain an internal temperature of 90° C. After about 6 hours at a temperature of 90° C., the conversion of the soybean oil is higher than 99%.

The reactor is left to cool to room temperature and 17.3 g of a solution of phosphoric acid at 85% by weight in water (0.15 moles of phosphoric acid) are added to neutralize the catalyst. The mixture is left under stirring for about 30 minutes and subsequently transferred to an apparatus consisting of a flask and a Claisen condenser where 368 g of a distillate having the following composition is removed, by distillation at a temperature of 80° C. and a reduced pressure of 15 mbar:

97.3% by weight of dimethyl carbonate, 2% by weight of methanol and 0.7% by weight of water.

Gaschromatographic analysis reveals the presence of 1% by weight of dimethyl carbonate (23.5 g) in the raw residual mixture, which is almost entirely removed by further distillation at a temperature of 90° C. and a pressure of 2 mbar for a period of 2 hours. The precipitate containing sodium monobasic phosphate, methylcarbonate of glycerol carbonate, glycerol carbonate and small quantities of methyl esters of fatty acids and esters of fatty acids of glycerol carbonate is filtered. The liquid raw mixture, having a weight of 2248.7 g, has the following composition, determined by means of HPLC and $^{13}$C NMR analyses:

24.8% by weight of esters of fatty acids of glycerol carbonate, 71.4% by weight of methyl esters of fatty acids, 1.2% by weight of glycerol carbonate, 1.8% by weight of methyl carbonate of glycerol carbonate, 0.17% by weight of diglycerides, 0.19% by weight of triglycerides and 0.4% by weight of dimethyl carbonate.

The methyl carbonate of glycerol carbonate is slowly separated by precipitation from the mixture obtained, which is liquid at room temperature.

This mixture can be used without any further treatment in the formulations of solvents which contain components capable of allowing the dissolution of the methyl carbonate of glycerol carbonate.

For all the other applications, the mixture was further purified.

EXAMPLE 2

Purification of the Raw Mixture

The raw mixture is diluted in a separating funnel with 1 liter of tert-butyl methyl ether (MTBE) and washed with three 500 ml portions of distilled water. The aqueous washings are then extracted with 500 ml of MTBE. The two organic phases in MTBE are combined and concentrated by distillation of the MTBE in a rotating evaporator at 80° C. and a minimum pressure of 15 mbar. Gaschromatographic analysis reveals the presence in the residual mixture of 1.5% by weight of MTBE, which is removed by further distillation at a temperature of 90° C. and a pressure of 2 mbar. The residual mixture, having a weight of 2113.8 g has the following composition, determined by means of HPLC and $^{13}$C NMR analyses:

25.6% by weight of esters of fatty acids of glycerol carbonate, 73.56% by weight of methyl esters of fatty acids, 0.4% by weight of methyl carbonate of glycerol carbonate, 0.07% by weight of glycerol carbonate, 0.17% by weight of diglycerides and 0.20% by weight of triglycerides.

This mixture is characterized by the following physicochemical properties:

| | |
|---|---|
| density (20° C.) (g/ml) | 0.904 |
| viscosity (20° C.) (Cst) | 9.7 |
| viscosity (40° C.) (Cst) | 5.6 |
| pour point (° C.) | −2 |
| flash point (° C.) (closed vase) | >120 |
| boiling point (° C.) (TGA) | >300 |
| sulfate ashes (weight %) | 0.0016 |
| interfacial pressure (20° C.) (mN/m) | 31.3 |
| acid number (mg KOH/Kg) | 0.3 |
| sodium content (mg/Kg) | <0.5 |
| phosphorous content (mg/Kg) | <3 |
| water (mg/Kg) | 200 |
| cetane number | 50.1 |
| gross heat value (MJ/Kg) | 38.77 |
| net heat value (MJ/Kg) | 36.305 |

EXAMPLE 3

The following reagents are added to the reactor described above, excluding the distillation column: 2034.5 g (2.33 moles) of soybean oil, 636 g (7.07 moles) of dimethyl carbonate and 16.7 g of 1,5,7-triazabicyclo[4.4.0]dec-5-ene (0.12 moles). The stirring is activated and the reactor is heated with an oil bath thermostat-regulated so as to have an internal temperature of 80° C. After about 6 hours at a temperature of 80° C., the conversion of soybean oil is higher than 99%.

The reactor is left to cool to room temperature. During the cooling, the reaction mixture is separated into two phases; a lower phase having a weight of 171.4 g and an upper phase having a weight of 2515.8 g. The lower phase has the following composition determined by means of HPLC and $^{13}$C NMR analyses:

9.7% by weight of 1,5,7-triazabicyclo[4.4.0]dec-5-ene, 12.9% by weight of dimethyl carbonate, 3.3% by weight of methanol, 28.9% by weight of glycerol carbonate, 26.9% by weight of methyl carbonate of glycerol carbonate, 1.5% by weight of bis carbonate of glycerol carbonate, 3.4% by weight of esters of fatty acids of glycerol carbonate and 13.4% by weight of methyl esters of fatty acids.

The upper phase is transferred to an apparatus consisting of a flask and a Claisen condenser where 340.8 g of dimethyl carbonate are removed, by distillation at a temperature of 80° C. and a reduced pressure of 15 mbar.

Gaschromatographic analysis reveals the presence of 1% by weight of dimethyl carbonate (21.8 g) in the raw residual mixture, which is almost entirely removed by further distillation at a temperature of 90° C. and a pressure of 2 mbar for a period of 2 hours. The raw mixture, having a weight of 2161.8 g, has the following composition, determined by means of HPLC and $^{13}$C NMR analyses:

23.6% by weight of esters of fatty acids of glycerol carbonate, 73.8% by weight of methyl esters of fatty acids, 0.5% by weight of glycerol carbonate, 1.4% by weight of methyl carbonate of glycerol carbonate, 0.16% by weight of diglycerides, 0.18% by weight of triglycerides and 0.4% by weight of dimethyl carbonate.

The methyl carbonate of glycerol carbonate is slowly separated by precipitation from the mixture obtained, which is liquid at room temperature.

This mixture can be used without any further treatment in the formulations of solvents which contain components capable of allowing the dissolution of the methyl carbonate of glycerol carbonate.

For all the other applications, the raw mixture must be further purified, using the procedure illustrated in Example II.

The mixture coming from the purification treatment, having a weight of 2053.7 g, has the following composition, determined by means of HPLC and $^{13}$C NMR analyses:

24% by weight of esters of fatty acids of glycerol carbonate, 75.2% by weight of methyl esters of fatty acids, 0.4% by weight of methyl carbonate of glycerol carbonate, 0.08% by weight of glycerol carbonate, 0.16% by weight of diglycerides, 0.19% by weight of triglycerides.

This mixture is characterized by the following physicochemical properties:

| | |
|---|---|
| density (20° C.) (g/ml) | 0.902 |
| viscosity (20° C.) (Cst) | 9.42 |
| viscosity (40° C.) (Cst) | 5.53 |
| pour point (° C.) | −2 |

| | |
|---|---|
| flash point (° C.) (closed vase) | >120 |
| boiling point (° C.) (TGA) | >300 |
| interfacial pressure (20° C.) (mN/m) | 30.9 |
| water content (mg/Kg) | 220 |
| cetane number | 49.0 |
| gross heat value (MJ/Kg) | 38.705 |
| net heat value (MJ/Kg) | 36.26 |

The invention claimed is:

1. A fuel, comprising one or more alkyl esters of fatty acids having formula (I):

RCOOR', one or more esters of fatty acids of glycerol carbonate having formula (II):

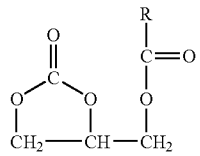

wherein:
R represents a mono- or polyunsaturated, linear, branched or cyclic alkyl or alkenyl radical, containing from 4 to 24 carbon atoms;
R' represents a linear, branched or cyclic alkyl radical containing from 1 to 8 carbon atoms, and
mineral gasoil, a fuel additive and mixtures thereof.

2. A method of making a fuel, the method comprising mixing mineral gasoil, a fuel additive and mixtures thereof with one or more alkyl esters of fatty acids having formula (I):

RCOOR' and one or more esters of fatty acids of glycerol carbonate having formula (II):

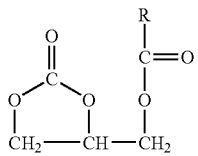

wherein:
R represents a mono- or polyunsaturated, linear, branched or cyclic alkyl or alkenyl radical, containing from 4 to 24 carbon atoms;
R' represents a linear, branched or cyclic alkyl radical containing from 1 to 8 carbon atoms.

3. The fuel of claim 1, wherein R represents a mono- or polyunsaturated, linear, branched or cyclic alkyl or alkenyl radical, containing from 8 to 22 carbon atoms; and R' represents a linear or branched alkyl radical containing from 1 to 4 carbon atoms.

4. The method of claim 2, wherein R represents a mono- or polyunsaturated, linear, branched or cyclic alkyl or alkenyl radical, containing from 8 to 22 carbon atoms; and R' represents a linear or branched alkyl radical containing from 1 to 4 carbon atoms.

5. The fuel of claim 1, wherein the esters of fatty acids of glycerol carbonate are present in a weight percentage ranging from 10 to 40%.

6. The method of claim 2, wherein the esters of fatty acids of glycerol carbonate are present in the fuel in a weight percentage ranging from 10 to 40%.

* * * * *